(12) United States Patent
Kitzer

(10) Patent No.: US 9,789,015 B2
(45) Date of Patent: Oct. 17, 2017

(54) FASTENERS

(71) Applicant: 3M INNOVATIVE PROPERTIES COMPANY, St. Paul, MN (US)

(72) Inventor: Peter Kitzer, Echt (NL)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 467 days.

(21) Appl. No.: 14/414,257

(22) PCT Filed: Jul. 12, 2013

(86) PCT No.: PCT/US2013/050201
§ 371 (c)(1),
(2) Date: Jan. 12, 2015

(87) PCT Pub. No.: WO2014/011957
PCT Pub. Date: Jan. 16, 2014

(65) Prior Publication Data
US 2015/0173981 A1 Jun. 25, 2015

(30) Foreign Application Priority Data
Jul. 12, 2012 (EP) .................................... 12176222

(51) Int. Cl.
*A61F 13/15* (2006.01)
*A61F 13/62* (2006.01)
(Continued)

(52) U.S. Cl.
CPC ........ *A61F 13/622* (2013.01); *A44B 18/0073* (2013.01); *A61F 13/15756* (2013.01);
(Continued)

(58) Field of Classification Search
CPC .. A61F 13/62; A61F 13/622; A61F 13/15756; A44B 18/0073
(Continued)

(56) References Cited

U.S. PATENT DOCUMENTS 198,097 A * 12/1877 Fries .................. B62C 11/00
24/580.11
207,253 A * 8/1878 Chipley ................. A44B 3/08
24/578.14
(Continued)

FOREIGN PATENT DOCUMENTS

| EP | 1452158 | 9/2004 |
| EP | 1902695 | 3/2008 |
| WO | WO 2012-015025 | 2/2012 |

OTHER PUBLICATIONS

International Search Report for PCT International Application No. PCT/US2013/050201 mailed on Sep. 18, 2013, 3 pages.

*Primary Examiner* — Jacqueline Stephens
(74) *Attorney, Agent, or Firm* — Steven A. Bern; Ted K. Ringsred

(57) ABSTRACT

The invention relates to fasteners comprising a flexible planar backing provided with a fastening element on its upper side and/or on its lower side, wherein the fastener consists of at least one generally Y-shaped one-piece section defined by two opposing arms, which are separated from each other by a recess, and by a third arm joined to the two opposing arms and extending away from said recess, wherein the shape and size of said third arm correspond to the shape and size of said recess.

13 Claims, 5 Drawing Sheets

(51) Int. Cl.
*A61F 13/56* (2006.01)
*A44B 18/00* (2006.01)

(52) U.S. Cl.
CPC .......... *A61F 13/5622* (2013.01); *A61F 13/62* (2013.01); *Y10T 24/2725* (2015.01)

(58) Field of Classification Search
USPC ................................ 604/396, 391, 387, 394
See application file for complete search history.

(56) References Cited

U.S. PATENT DOCUMENTS 3,620,180 A * 11/1971 Waldes ...................... A41F 1/04
  112/407
4,713,864 A * 12/1987 Hess ..................... A44C 5/2057
  24/589.1

* cited by examiner

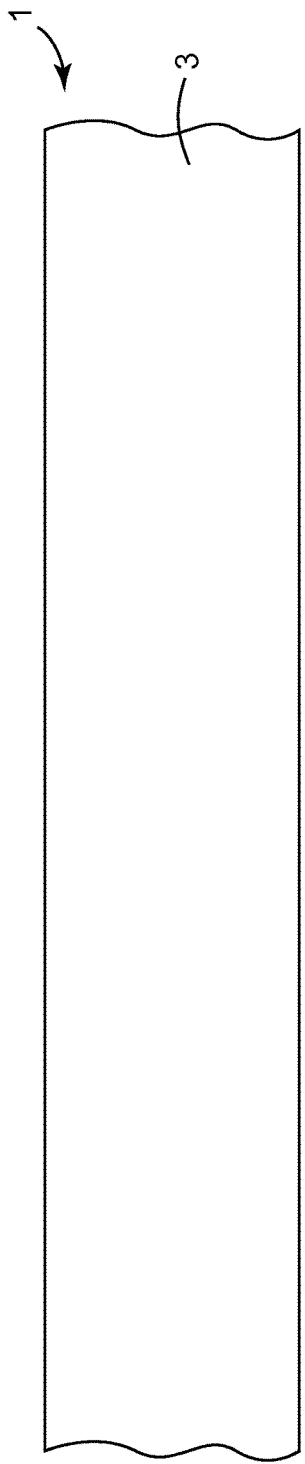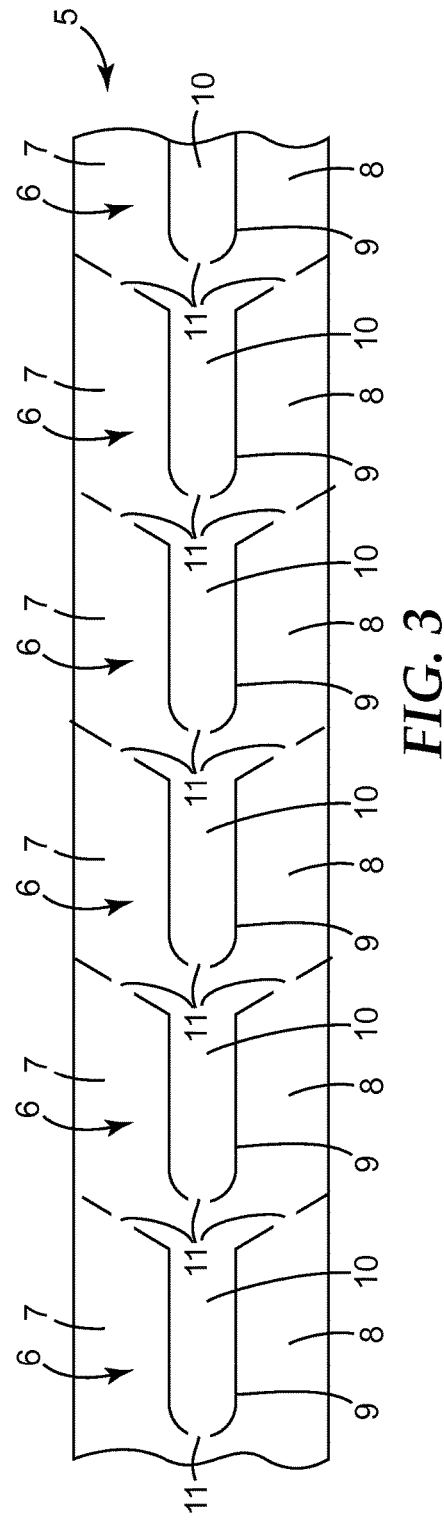

FASTENERS

CROSS REFERENCE TO RELATED APPLICATIONS

This application is a national stage filing under 35 U.S.C. 371 of PCT/US2013/050201, filed Jul. 12, 2013, which claims priority to European Application No. 12176222.3, filed Jul. 12, 2012, the disclosure of which is incorporated by reference in its/their entirety herein.

FIELD OF THE INVENTION

The present invention relates to fasteners, webs comprising a plurality of such fasteners which are successively arranged, and absorbent articles comprising at least one of such fasteners.

BACKGROUND OF THE INVENTION

Some male incontinence guards, such as those sold under the trade name Tena for Men™ level 1 or level 2, have a body side liner, an outer liner and an absorbent pad disposed therebetween. The guard is generally triangular shaped when laid out flat. The base of the triangle is worn closer to the waist of the user, while the point of the triangle is positioned more towards the area between the legs of the user. This shape of article is more comfortable for the wearer and offers liquid retention benefits. The outer liner has fastening elements in the form of rectangular strips of adhesive tape attached to it that are covered by a release liner. To wear, the release liner is peeled away and the adhesive strips serve to removably fix the guard in position on the underpants of the wearer. Alternative shapes for the adhesive tapes may be desirable that provide improved fastening coverage for such triangular-shaped absorbent articles. Such alternative shapes would optimally maintain material use efficiency (lack of waste trimmings) of rectangular strips.

SUMMARY OF THE INVENTION

It has been found that it may be desirable to form a Y-shape fastener or the like. Such a Y-shape is defined by two opposing arms which are separated from each other by a recess, and by a third arm extending in extension of and away from said recess. Such a Y-shape will provide coverage of the corner portions of a triangle shaped guard by a single fastening element.

A problem with cutting a complex shape such as a Y-shape or the like is that it involves a significant amount of waste material as a result of a nesting mismatch in adjacent elements. Stamping such complex shapes out of a web of material results in too much waste for production efficiency purposes. Accordingly, it would be desirable to provide a fastener that can be produced with reduced waste.

In order to solve this object, the present invention provides a fastener comprising a flexible planar backing and a fastening element on its upper side and/or on its lower side, wherein the fastener has at least one generally Y-shaped one-piece section defined by two opposing arms, which are separated from each other by a recess, and by a third arm joined to the two opposing arms and extending away from said recess, wherein the shape and size of said third arm correspond to the shape and size of said recess. This construction allows for successive fasteners to be stamped out of a web of material without producing any waste.

The outer edges of the opposing arms preferably extend parallel to each other. Accordingly, the elements can be stamped out of a strip or roll of web material having parallel side edges.

The recess as well as the third arm may have any shape, e. g. a generally rectangular, or triangular, polygonal, generally curved such as, e.g., semi-circular, and/or exhibit a more complex contour. This reduces the complexity of the stamping tool.

The bottom of the recess, as well as the free corresponding end of the third arm, may comprise a widened portion. Such a widened portion improves the attachment of the free end of the third arm of fastener to an article, such as an absorbent article.

According to one aspect of the present invention the backing is made of flexible thermoplastic resin, in particular resiliently flexible thermoplastic resin so that the fastener can easily conform to the shape of the article to which the fastening element is affixed.

Preferably each fastener element is chosen from the group comprising hook members of a hook and/loop fastener, loop members of a hook-and-loop fastener and/or an adhesive coating.

According to one aspect of the present invention the fastener consists of a plurality of adjacently arranged Y-shaped sections formed as a single piece, wherein one of the opposing arms of a first Y-shaped section also forms one of the opposing arms of an adjacent Y-shaped section.

Moreover, the present invention provides a web comprising a plurality of successively arranged fasteners of the above-mentioned type, wherein the fasteners are completely cut out apart from bridging segments which connect adjacent fasteners with each other. Such webs can be delivered to a producer of articles, such as absorbent articles, where the single fasteners are severed from the web and fixed to the articles.

In one embodiment, the web is in the form of a strip. This simplifies further processing.

In an alternative embodiment, the web is in the form of a roll in order to facilitate the transport and packaging of the web.

Furthermore, the present invention provides an absorbent article comprising at least one fastener of the above-mentioned type.

Moreover, the present invention relates to a method of providing a plurality of individual fasteners according to the present invention comprising the steps of
  providing a web of pre-cut fasteners which are completely cut out apart from severable bridging elements, and
  individualizing said fasteners from said web by severing said bridges.

The present invention also relates to a method of making absorbent articles comprising the steps of
  providing a web of absorbent articles,
  providing a plurality of fasteners according to the present invention, and
  applying said fasteners to said absorbent articles.

The present invention provides for an essentially wasteless method of providing integral fasteners. The fasteners of the present invention exhibit when applied to absorbent articles such as diapers, feminine hygiene articles such as feminine napkins or male incontinence guards, respectively, an improved stress distribution and/or an improved flexibility thereby distinctly improving the performance of the absorbent article.

BRIEF DESCRIPTION OF THE FIGURES

FIG. 1 is a plan view of a web, from which a web of fasteners according to an embodiment of the present invention is produced;

FIG. 2 is a side view of the web in FIG. 1;

FIG. 3 is a web of fasteners, according to a first embodiment of the present invention, produced from the web in FIGS. 1 and 2;

DETAILED DESCRIPTION OF PREFERRED EMBODIMENTS OF THE INVENTION

Figure 4:
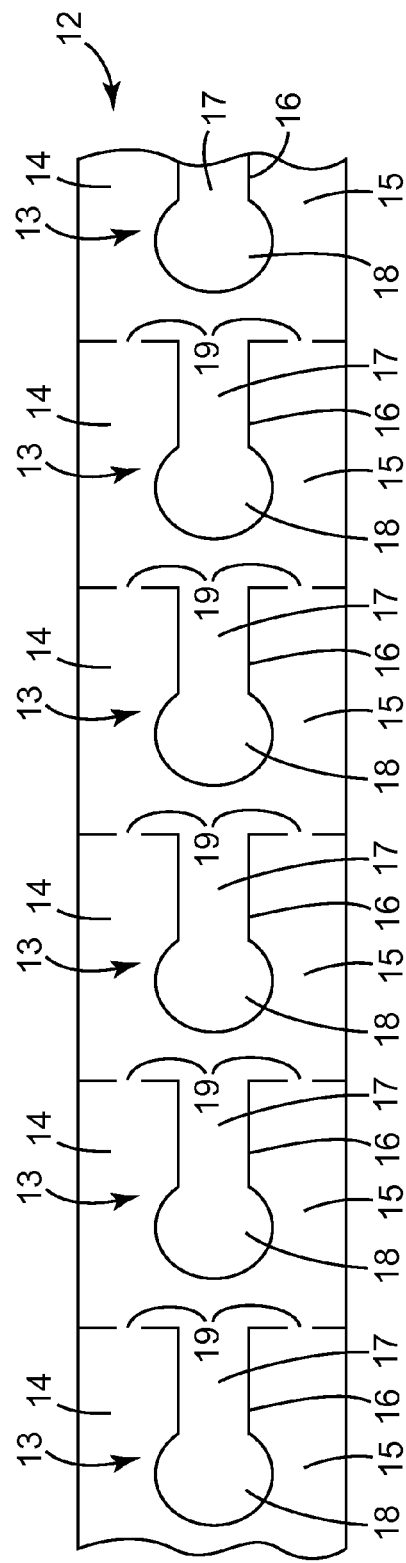
FIG. 4 is a plan view of a web of fasteners, according to a second embodiment of the present invention, produced from the web in FIGS. 1 and 2.

FIGS. 1 and 2 show a strip of web 1 with parallel side edges from which fasteners according to the present invention may be produced. The web 1 comprises a flexible planar backing 2, which is made of a flexible thermoplastic resin, in particular resiliently flexible thermoplastic resin. The upper side and the lower side of the backing 2 may both be provided with a fastening element 3 and 4 each chosen independently from each other from a group comprising hook members of a hook-and-loop fastener, loop members of a hook-and-loop fastener or an adhesive coat. For example, the fastening element 3 on the upper side of the backing 2 may be an adhesive coat, which may be covered by a release liner even though not shown here, and the fastening element 4 on the lower side of the backing 2 comprises a plurality of hook members of a hook-and-loop fastener, each hook member having a stem portion and may have a head portion, wherein the hook members are capable of being engaged with corresponding loop members of a hook-and-loop fastener or directly with garment like underwear. The web 1 can be supplied in roll form.

FIG. 3 shows a web of fasteners 5, according to a first embodiment of the present invention, which can be produced from the precursor web shown in FIGS. 1 and 2 by means of die cutting or the like whereby the fasteners remain severably connected via bridging segments 11. Accordingly, also the web of fasteners 5 comprises the backing 2, the fastening element 3 and the optional fastening element 4. The web of fasteners 5 comprises a plurality of successively arranged fasteners 6, wherein each fastener 6 consists of a generally Y-shaped one-piece section. This Y-shaped one-piece section is defined by two opposing arms 7 and 8 which are separated from each other by a recess 9, and by a third arm 10 joined to the two opposing arms 7 and 8 and extending away from said recess 9, wherein the shape and size of said third arm 10 correspond to the shape and size of said recess 9. The arms 7 and 8 extend parallel to each other, and the recess 9 as well as the third arm 10 have a generally rectangular contour. Each fastener 6 is completely cut out from the web 1 apart from bridging segments 11, which connect adjacent fastener 6 with each other, so that the web of fasteners 5 still forms a continuous strip. The bridging elements can be formed, for example, by perforations or other weakening lines.

FIG. 4 shows a web of fasteners 12, according to a second embodiment of the present invention, which is made from the web 1 in FIGS. 1 and 2 by means of die-cutting or the like. Accordingly, also the web of fasteners 12 comprises a backing 2, a fastening element 3 and an optional fastening element 4. Similar to the web of fasteners 5 in FIG. 3 the web of fasteners 12 in FIG. 4 comprises a plurality of successively arranged fasteners 13, wherein each fastener 13 consists of a single generally Y-shaped one-piece section. Each generally Y-shaped one-piece section is defined by two opposing arms 14 and 15, which are separated from each other by a recess 16, and by a third arm 17 joined to the two opposing arms 14 and 15 and extending away from the recess 16, wherein the shape and size of said third arm 17 correspond to the shape and the size of the recess 16. The arms 14 and 15 extend parallel to each other. The recess 16 as well as the arm 17 generally essentially have a key-hole type contour wherein the bottom of the recess 16 as well as the free corresponding end of the third arm 17 comprise a widened portion 18 of generally circular shape as shown in the figures. Other shapes such as essentially rectangular, triangular, polygonal, generally curved such as, e.g., semi-circular and combinations of the aforementioned shapes are also conceivable. Each fastener 13 is completely cut out apart from bridging segments 19, which connect adjacently arranged fasteners 13 with each other.

Figure 5:
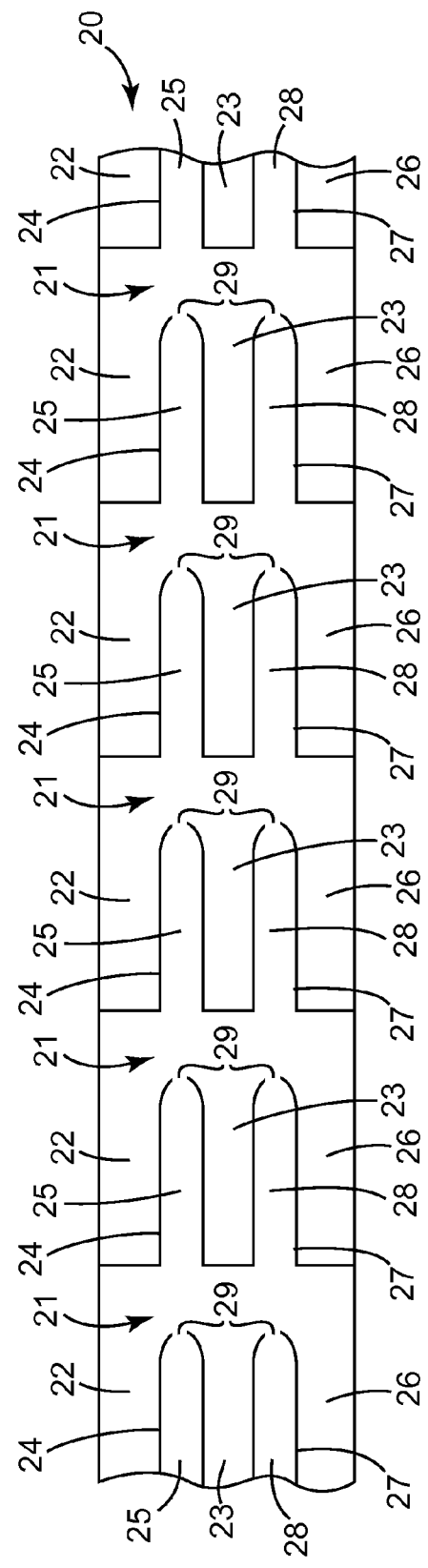
FIG. 5 is a plan view of a web of fasteners, according to a third embodiment of the present invention, produced from the web in FIGS. 1 and 2.

FIG. 5 shows a web of fasteners 20, according to a third embodiment of the present invention, which is made from the web 1 in FIGS. 1 and 2 by means of die cutting or the like. Accordingly the web of fasteners 20 also comprises a backing 2 as well as a fastening element 3 and an optional fastening element 4. The web of fasteners 20 has a plurality of successively arranged fasteners, wherein each fastener 21 consists of two generally Y-shaped sections formed as single piece. The first Y-shaped section is defined by two opposing arms 22 and 23, which are separated from each other by a recess 24, and by a third arm 25 joined to the two opposing arms 22 and 23 and extending away from said recess 24, wherein the shape and size of said third arm 25 correspond to the shape and size of said recess 24. The second Y-shaped section is defined by two opposing arms 23 and 26, which are also separated from each other by a recess 27, as well as by an arm 28 joined to the two opposing arms 22 and 23 and extending away from said recess 27, wherein the shape and size of said arm 28 correspond to the shape and size of said recess 27. Accordingly, one of the opposing arms of the first Y-shaped section also forms one of the opposing arms of the adjacent Y-shaped section, namely the arm 23. The fasteners 21 are completely cut out apart from bridging segments 29, which connect adjacent fasteners 21 with each other.

It should be noted that the number of Y-shaped sections forming one fastener 21 can be varied as needed.

Figure 6:
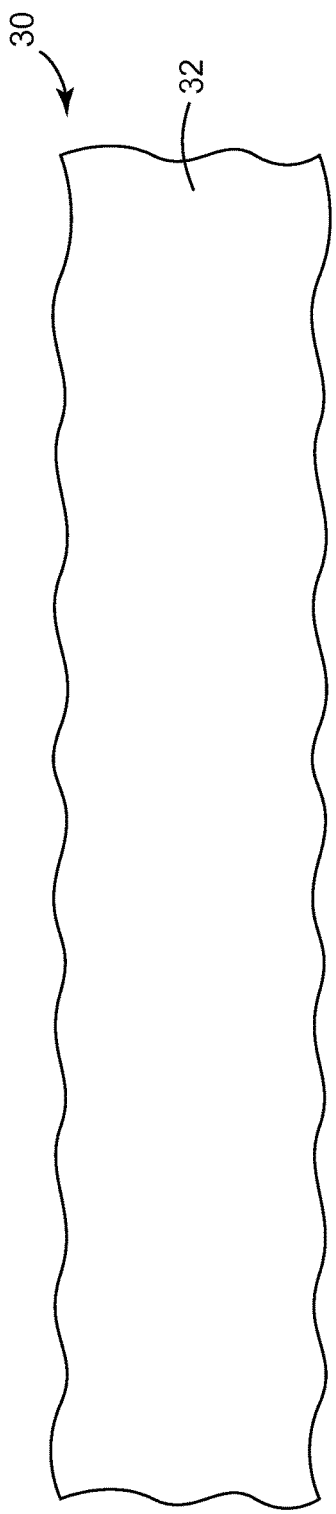
FIG. 6 is a plan view of another web.
Figure 7:
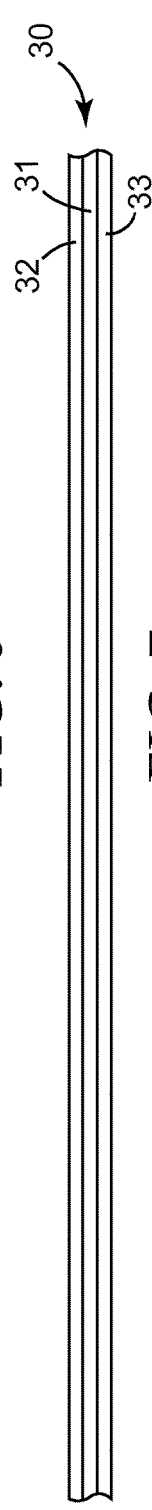
FIG. 7 is a side view of the web in FIG. 6.

FIGS. 6 and 7 show a web 30 comprising a flexible planar backing 31 made of a flexible thermoplastic resin, in particular resiliently flexible thermoplastic resin. The backing 31 is provided on its upper side and on its lower side with fastening elements 32 and 33, each chosen from the group comprising hook members of a hook-and-loop fastener, loop members of a hook-and-loop fastener or an adhesive coat. In contrast to the web 1 in FIGS. 1 and 2, the side edges of the web 30 may not be straight lines but have a regular or irregular curved form such as a sinusoidal form and/or regular or irregular polygonal form such as saw-tooth or zig-zag form.

Figure 8:
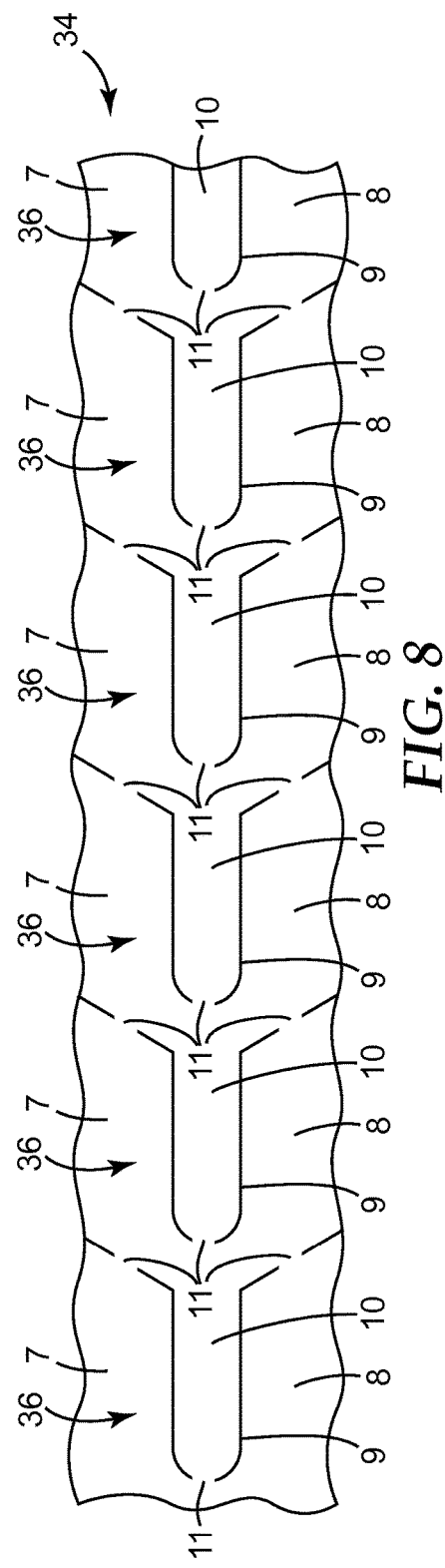
FIG. 8 is a plan view of a web of fasteners, according to a fourth embodiment of the present invention, produced from the web in FIGS. 6 and 7.

FIG. 8 shows a web of fasteners 34, according to a fourth embodiment of the present invention, which is made from the web 30 in FIGS. 6 and 7. The web of fasteners 34 comprises a plurality of successively arranged fasteners 36. The form and shape of each fastening element 36 generally correspond to the shape and size of the fasteners 6 in FIG. 3, for which reason same reference numerals are used for corresponding features. However, in contrast to the fastener 6 shown in FIG. 3, the sides 7, 8 of the fastener 36 are waved due to the wave form of the starting web 30 in FIG. 6.

Figure 9:
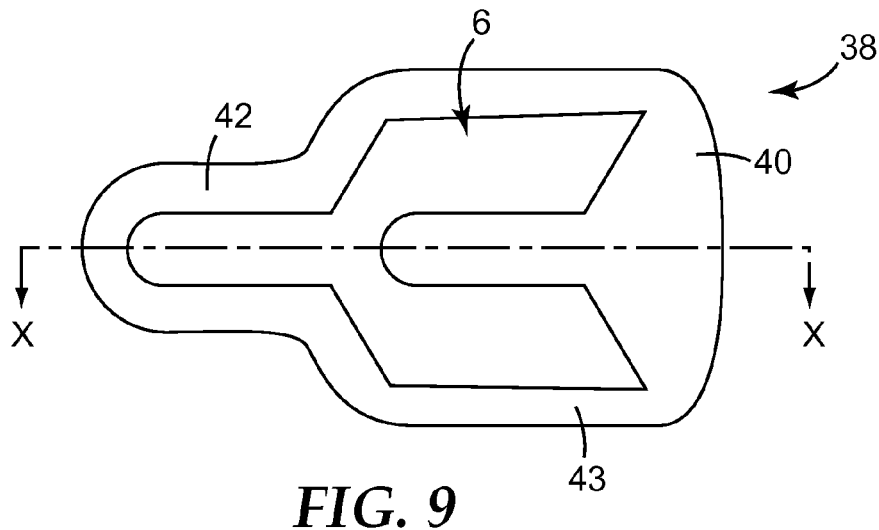
FIG. 9 is a bottom view of an absorbent article according to an embodiment of the present invention.
Figure 10:
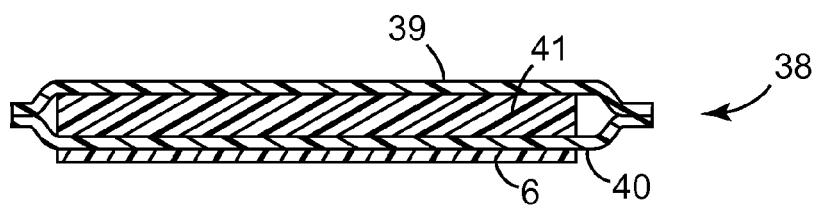
FIG. 10 is a sectional side view of the absorbent article in FIG. 9.

FIGS. 9 and 10 show an absorbent article 38 according to a first embodiment of the present invention, which defines a male incontinence guard. The absorbent article 38 comprises a body side liner 39, an outer liner 40 and an absorbent pad 41 disposed therebetween. The absorbent article 38 has a narrow portion 42 and a wide portion 43 when laid out flat. The wide portion 43 is worn closer to the waist of the user, while the narrow portion 42 is positioned more towards the area between the legs of the user. This shape of the absorbent article 38 is comfortable for the wearer and offers liquid retention benefits. On the outer liner 40 a fastener 6 of the type shown in FIG. 3 is attached. More precisely, an adhesive fastening element 4, after peeling off an optional release liner, is affixed to the outer liner 40, such that a hook-type fastening element 3 faces outwards in order to removably fix the absorbent article 38 in position on the underpants of a wearer.

Figure 11:
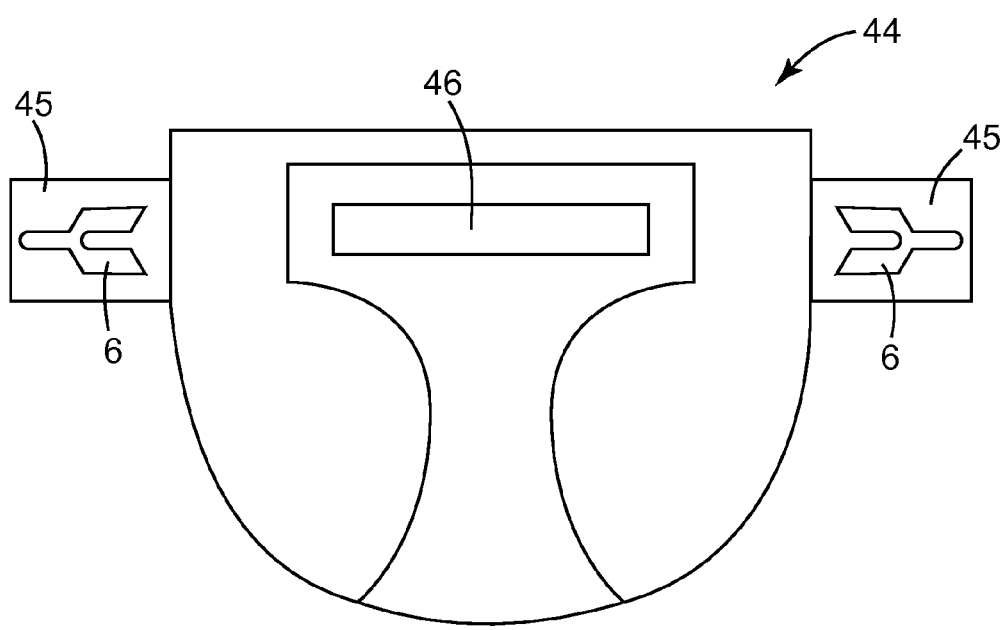
FIG. 11 is a front view of another absorbent article according to the present invention.

FIG. 11 shows another absorbent article 44 according to an embodiment of the present invention, which defines a conventional diaper for an infant. The general configuration of such a diaper is already known in the art, wherefore it is not described in detail here. Fasteners 6 of the kind shown in FIG. 3 are affixed to elastic strips 45 of the diaper 44, such that hook members of the fastening elements 4 face outward to be brought into contact with corresponding loop members 46 affixed to the absorbent article 44. Accordingly, the diaper can be opened and closed by means of the hook-and-loop fasteners.

Figure 12:
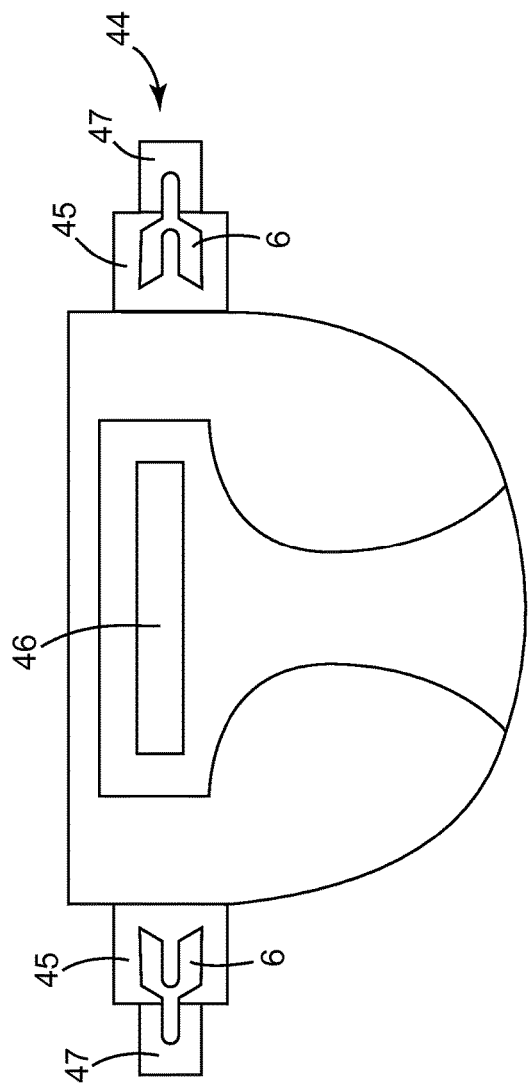
FIG. 12 is a front view of another embodiment of an absorbent article according to the present invention.

FIG. 12 shows a diaper as a further embodiment of an absorbent article 44 according to the present invention. It is similar to the embodiment of FIG. 11 but differs in that an elastic fastening tap 47 is attached to the elastic strips 45 wherein the fastener 6 is attached to both the elastic strips 45 and the additional fastening tab 47.

Figure 13:
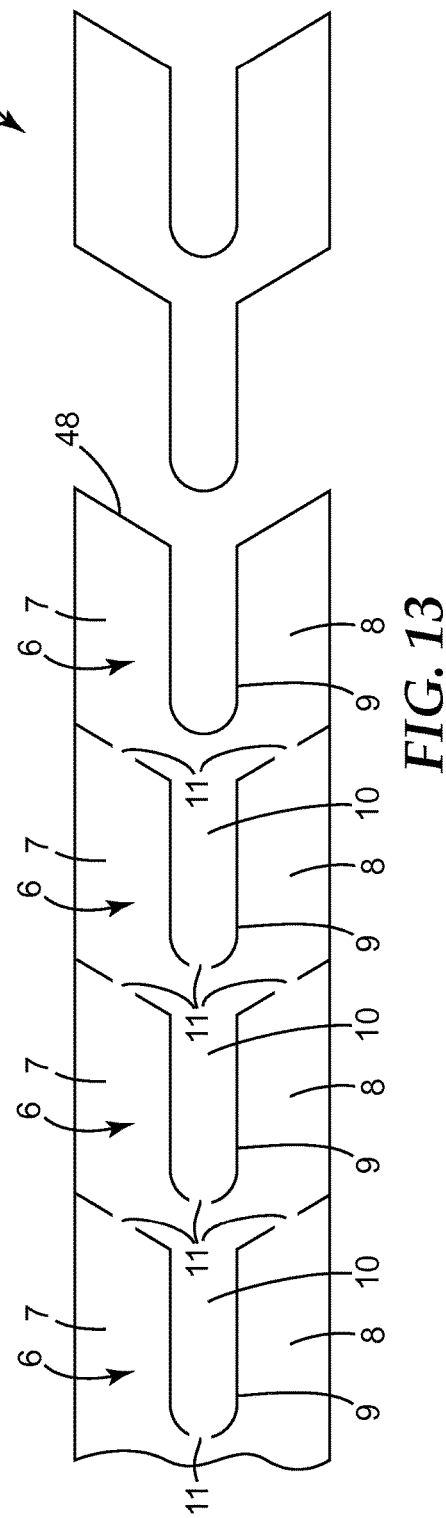
FIG. 13 is a top view on a web according to the present invention illustrating a process of individualizing fasteners from said web.

FIG. 13 illustrates the method of separating individual fasteners 6 from the web 1 of fasteners 6. In the web 1 the fasteners 6 are completely cut out apart from severable bridging segments 11. The fasteners 6 are individualized by breaking up the bridging elements 11 thereby severing the individual fastener 6 from the remainder of the web 1.

The invention claimed is:

1. A fastener comprising a flexible planar backing provided with a fastener element on its upper side and/or on its lower side, wherein the fastener consists of at least one generally Y-shaped one-piece section defined by two opposing arms, which are separated from each other by a recess, and by a third arm joined to the two opposing arms and extending away from said recess, wherein the shape and size of said third arm correspond to the shape and size of said recess.

2. The fastener according to claim 1, wherein the outer edges of the opposing arms extend parallel to each other.

3. The fastener according to claim 1, wherein the recess as well as the third arm generally have a generally rectangular contour.

4. The fastener according to claim 1, wherein the bottom of the recess as well as the free corresponding end of the third arm comprise a widened portion.

5. The fastener according to claim 1, wherein the backing is made of a flexible thermoplastic resin.

6. The fastener according to claim 1, wherein each fastening element is selected from the group comprising hook members of a hook-and-loop fastener, loop members of a hook-and-loop fastener and an adhesive coat.

7. The fastener according to claim 1, wherein the element consists of a plurality of adjacently arranged Y-shaped sections formed as a single piece, wherein one of the opposing arms of a first Y-shaped section also forms one of the opposing arms of an adjacent Y-shaped section.

8. A web of fasteners comprising a plurality of successively arranged fasteners according to claim 1, wherein the fasteners are completely cut out apart from severable bridging segments, which connect adjacent fasteners with each other.

9. The web of fasteners according to claim 8, wherein the web is a strip.

10. A roll of fasteners according to claim 8.

11. A method of providing a plurality of individual fasteners, the method comprising the steps of
providing a web of fasteners according to claim 8, and
individualizing said fasteners by severing them from said web.

12. An absorbent article (38; 44) comprising at least one fastener according to claim 1.

13. A method of making absorbent articles comprising at least one fastener according to claim 1, the method comprising the steps of
providing a web of absorbent articles,
providing a plurality of fasteners according to claim 1, and
applying said fasteners to said absorbent articles.

* * * * *